United States Patent [19]
Brown

[11] Patent Number: 5,423,427
[45] Date of Patent: Jun. 13, 1995

[54] DENTAL TRAVEL PACK

[76] Inventor: Janice M. Brown, 3724 Spencer St. #327, Torrance, Calif. 90503

[21] Appl. No.: 235,865

[22] Filed: May 2, 1994

[51] Int. Cl.⁶ .................. B65D 85/20; A46B 17/00
[52] U.S. Cl. ....................... 206/581; 132/311; 206/362.2; 206/369
[58] Field of Search ............ 15/146, 167.1, 167.2; 132/308–311, 328; 206/15.2, 361, 362, 362.1, 369, 362.2, 581

[56] References Cited

U.S. PATENT DOCUMENTS

| | | | |
|---|---|---|---|
| 835,365 | 11/1906 | Morgan | 132/311 |
| 902,796 | 11/1908 | Archer et al. | 132/311 |
| 2,168,689 | 8/1939 | Smith et al. | 132/311 |
| 2,701,052 | 2/1955 | Martel | 206/377 |
| 3,763,869 | 10/1973 | Sanders | 132/311 |
| 4,542,828 | 9/1985 | Gotto | 206/581 |
| 4,756,405 | 7/1988 | Crozier | 206/362 |
| 4,924,547 | 5/1990 | Wachtel et al. | 132/311 |
| 5,095,924 | 3/1992 | Stanfield | 206/581 |

FOREIGN PATENT DOCUMENTS

| | | | |
|---|---|---|---|
| 0641525 | 8/1928 | France | 132/308 |
| 2706062 | 8/1978 | Germany | 206/362.2 |

Primary Examiner—Jimmy G. Foster

[57] ABSTRACT

A pocket size dental travel pack which comprises a rectangular, resilient plastic carrying compartment having one face hinged at the side thereof to permit opening at least 90 degrees to completely expose the interior of said compartment; a plurality of dental care implements mounted within and rotatably extendable vertically from said compartment, said implements when rotated into the vertical position being locked into such position by the closing of said hinged face; said compartment forming a handle for using said implements when in the vertical position.

5 Claims, 4 Drawing Sheets

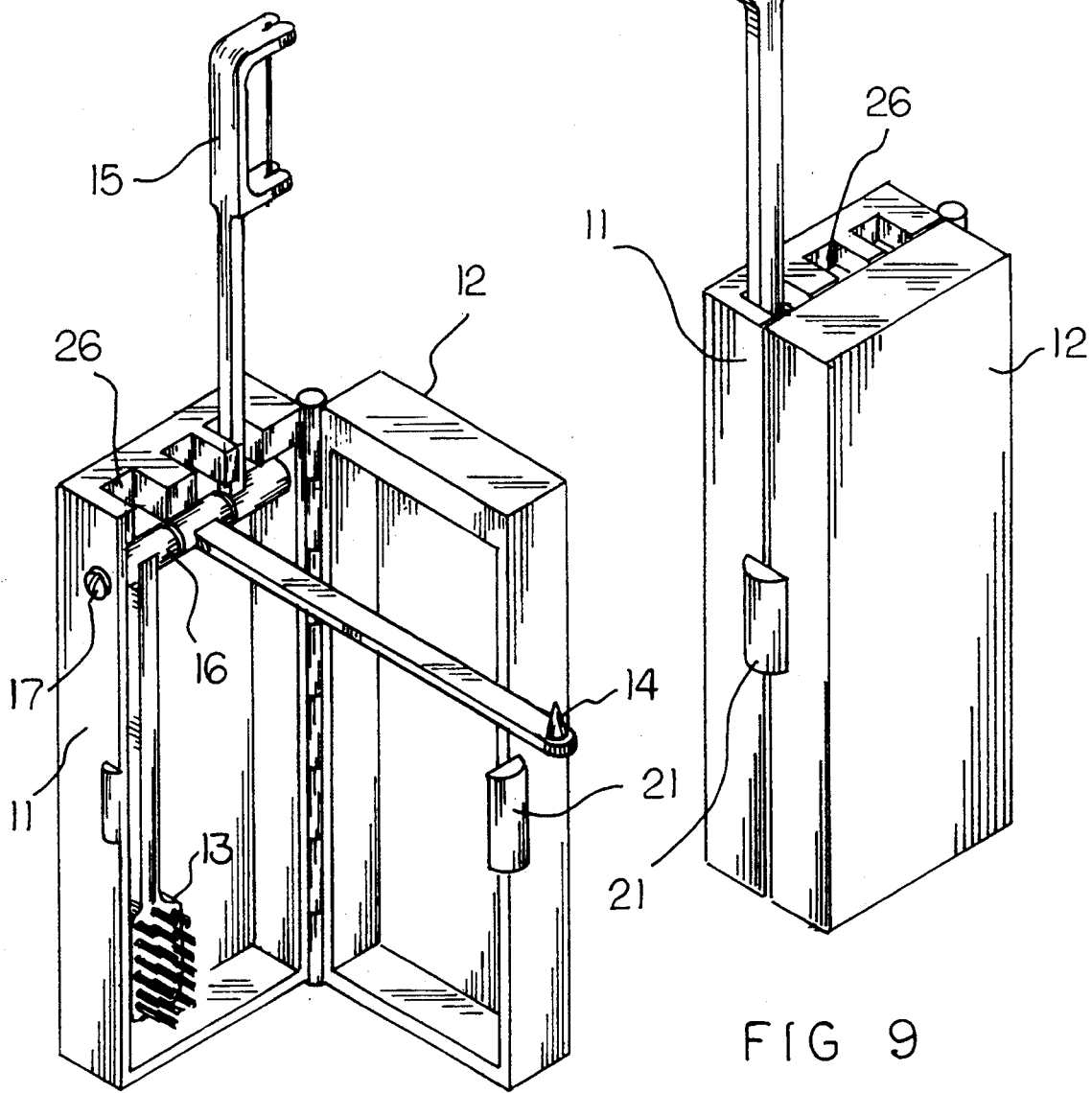

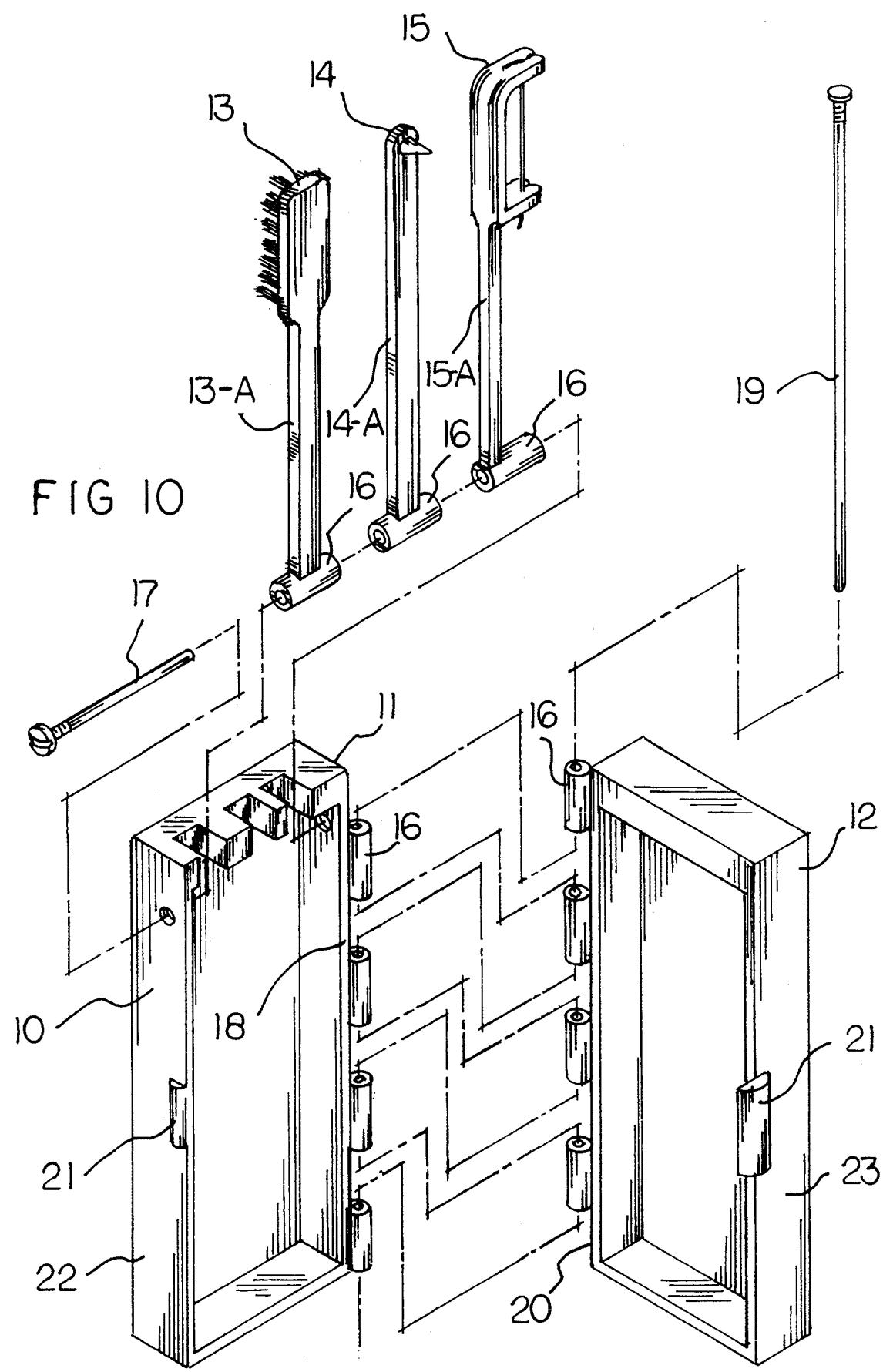

DENTAL TRAVEL PACK

BACKGROUND OF THE INVENTION

1. Field of the Invention

The present invention relates to dental care and more particularly pertains to a travel pack which may be used to carry a plurality of dental care implements in a pocket-size case and to readily permit the use thereof without fear of misplacing or losing any individual implement.

2. Description of the Prior Art

The use of travel toothbrushes and the like is known in the prior art. More specifically, devices heretofore devised and utilized for the purpose of dental care while traveling are known to consist basically of familiar, expected and obvious structural configurations, notwithstanding the myriad of designs encompassed by the crowded prior art which have been developed for the fulfillment of countless objectives and requirements. Most consist merely of containers for a dental implement such as a brush where the implement must be removed from the container, be affixed thereto in some fashion for use and then be manually disconnected and returned to the container for transport. Since the implement is normally free of the case, the danger of losing or misplacing it exists, and the problem of affixing it to the container (which usually acts as a handle) may prove difficult and/or annoying. Typical of such prior art devices are those illustrated in U.S. Letters Pat. Nos. 5,152,307; 4,628,949; 4,865,481; and 4,002,181.

In this respect, the dental travel pack according to the present invention substantially departs from the conventional concepts and designs of the prior art, and in so doing provides an apparatus primarily developed for the purpose of safely, conveniently and quickly transporting a plurality of dental care implements, putting them to use and returning them to storage.

Therefore, it can be appreciated that there exists a continuing need for a new and improved dental travel kit which can be conveniently used. In this regard, the present invention substantially fulfills this need.

SUMMARY OF THE INVENTION

In view of the foregoing disadvantages inherent in the known types of dental travel devices now present in the prior art, the present invention provides an improved dental travel pack wherein the same can be utilized to conveniently transport and use a plurality of dental care implements. As such, the general purpose of the present invention, which will be described subsequently in greater detail, is to provide a new dental travel pack which has many of the advantages of the devices mentioned heretofore and many novel features that result in a dental travel unit which is not anticipated, rendered obvious, suggested, or even implied by any of the prior art devices, either alone or in any combination thereof.

To attain this, the present invention generally relates to a pocket size dental travel pack which comprises a rectangular, resilient plastic carrying compartment having one face hinged at the side thereof to permit opening at least 90 degrees to completely expose the interior of said compartment; a plurality of dental care implements mounted within and rotatable extendable vertically from said compartment, said implements when rotated into the vertical position being locked into such position by the closing of said hinged face; said compartment forming a handle for using said implements when in the vertical position.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new dental travel pack which has many of the advantages of the devices mentioned heretofore and many novel features that result in a pack which is not anticipated, rendered obvious, suggested, or even implied by any of the prior art devices, either alone or in any combination thereof.

It is another object of the present invention to provide a new and improved dental travel pack which may be easily and efficiently manufactured and marketed.

It is a further object of the present invention to provide a new and improved dental travel pack which is of a durable and reliable construction.

An even further object of the present invention is to provide a new and improved dental travel pack which is susceptible of a low cost of manufacture with regard to both materials and labor, and which accordingly is then susceptible of low prices of sale to the consuming public, thereby making such units economically available to the buying public.

Still another object of the present invention is to provide a new and improved dental travel pack containing a plurality of dental care implements.

Yet another object of the present invention is to provide a new and improved dental travel pack where the implements carried therein are secured against misplacement or loss.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 8 is a perspective view of the present invention with the implements shown in FIGS. 1 through 7 installed therein and with a hinged face of the carry pack open.

FIG. 9 is a perspective view of the device in FIG. 8 with the face closed and one of the implements locked into the use position.

FIG. 10 is an exploded perspective view of the present invention.

DESCRIPTION OF THE PREFERRED EMBODIMENT

Figure 1:
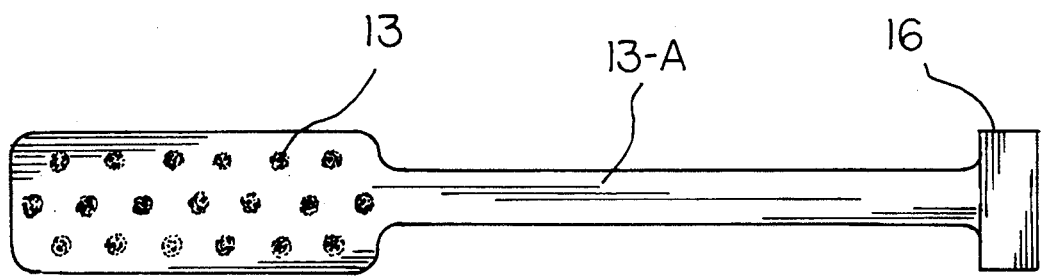
FIG. 1 is a top plan view of a toothbrush used in the present invention.

With reference now to the drawings, and in particular to FIG. 10 thereof, a new and improved dental travel pack embodying the principles and concepts of the present invention and generally designated by the reference numeral 10 will be described.

More specifically, it will be noted that FIG. 10 illustrates the present invention 10 in an exploded format while FIGS. 1 through 7 depict some of the elements shown in FIG. 10. The present invention 10 comprises a resilient plastic carrying case or compartment 11 having a hinged side face 12 which may be opened at least 90 degrees (or as shown in this view completely removable from the rest of compartment 11). Pivotally mounted in compartment 11 are a plurality of dental care implements 13, 14 and 15 (shown in detail in FIGS. 1 through 7). These implements have the usual, conventional shafts 13A, 14A and 15A but terminate in a tubular pivot number 16 adapted to receive a pivot pin 17 extending into and through compartment 11 said pivot pin 17 having a head arranged to project exteriorly of the carrying case when the pivot pin 17 is directed through the carrying case.

The dental implements include a brush head for implement 13, a massage tip for implement 14, and a dental floss holder implement 15. The top or upper face of compartment 11 is notched to receive shafts 13A, 14A and 15A when they are swung upwardly therein. Similar tubular pivot members 16 are provided in spaced relationship on the side 18 of compartment 11 to receive a pivot pin 19 extending downwardly therethrough and also through a similar set of tubular pivot members 16 on the edge 20 of side face 12 to hinge such side face 12 to compartment 11. A frictional snap catch 21 having one portion face thereof on the side 22 of compartment 11 and the other portion on the side 23 of hinged face 12 serves to keep the compartment 11 in closed position when desired.

Referring now to FIGS. 1 through 7, the dental implements 13-15 shown in FIG. 10 are illustrated in detail.

Figure 2:
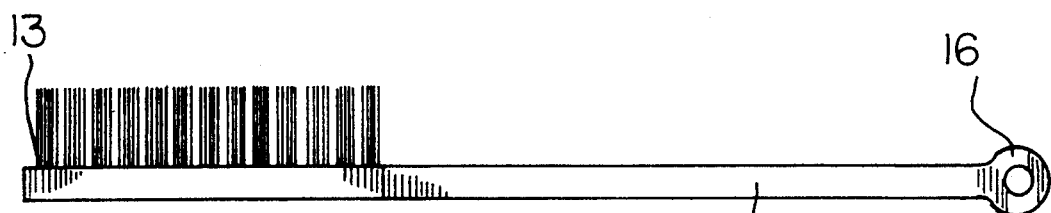
FIG. 2 is a side plan view of the brush of FIG. 1.

FIGS. 1 and 2 illustrate a toothbrush 13 configured for use in the present invention. The brush 13 has a flat shaft 13A extending from the brush 13 and terminating in the tubular pivot member 16 as described in connection with FIG. 10.

Figure 3:
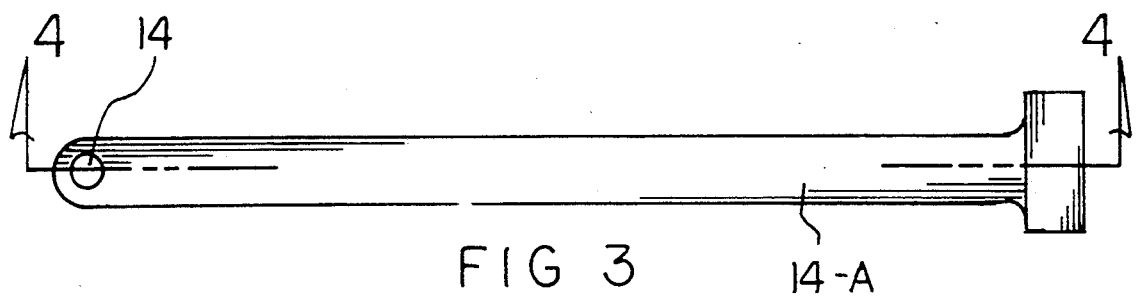
FIG. 3 is a top plan view of a flexible dental pack for use in the present invention.
Figure 4:
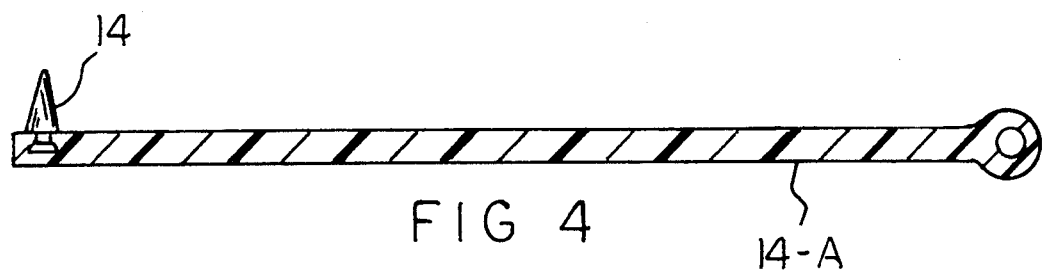
FIG. 4 is a sectional view on line 4—4 of FIG. 3.

FIGS. 3 and 4 show a dental pick 14 with a similar flat shaft 14A terminating in the pivot member 16.

Figure 5:
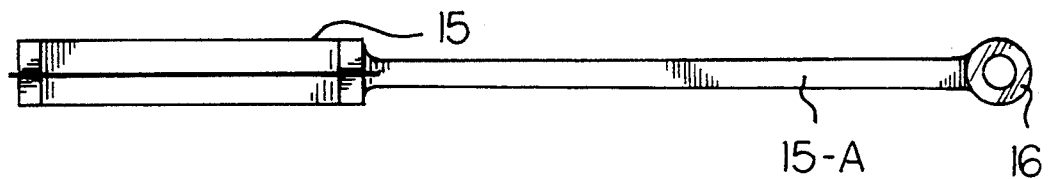
FIG. 5 is a top plan view of a dental flossing unit for use in the present invention.
Figure 6:
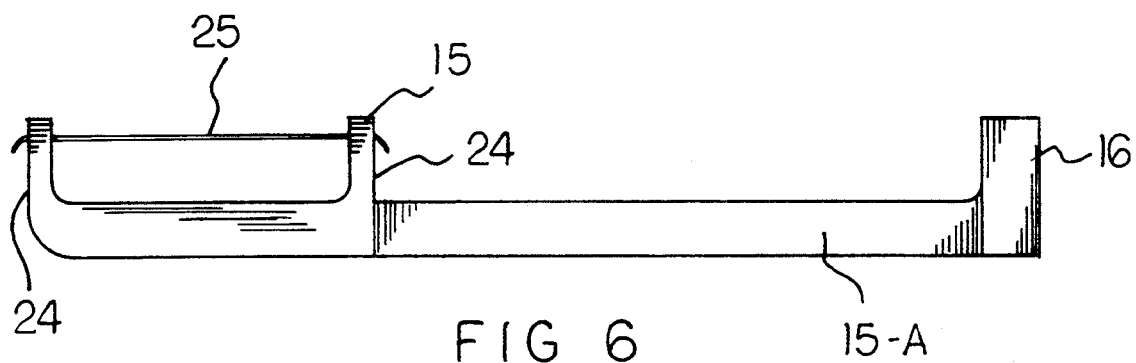
FIG. 6 is a side plan view of the flossing unit of FIG. 5.
Figure 7:
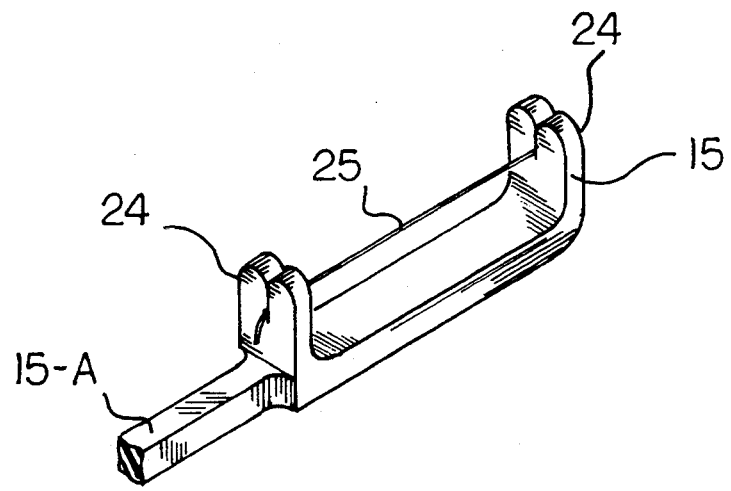
FIG. 7 is a perspective view of the unit of FIG. 5 and 6.

FIGS. 5 through 7 show a flossing head 15 with the same type shaft 15A and pivot member 16 as shown in FIGS. 1 through 4. The head 15 itself is of conventional design comprising a pair of upstanding flanges 24 removably supporting therebetween a length of dental floss 25.

FIGS. 8 and 9 illustrate the use of the dental pack 10. In FIG. 8, the compartment 11 is shown in open position with one of the dental implements, flossing head 15, swung up into operative position extending vertically through one of the notches 26 in the top of compartment 11. In this drawing, the dental pick 14 is shown swung partially out of container 11 illustrating that the implements 13, 14 and 15 are pivoted through the engagement of pivot member 16 with pivot pin 17. Toothbrush 13 is shown in its stored or travel position within container 11.

FIG. 9 shows the toothbrush 13 swung up into operative position where it is held vertically extending from notch 26 in container 11 by the closed hinged face 12. Snap catch 21 keeps container 11 closed until deliberately released when the unit is to be changed to put a different implement in use or when all implements are to be put within container 11 for transport.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art., it is not desired to limit the invention to the exact construction and operation shown and described, and accordingly, all suitable modifications and equivalents may be resorted to, falling within the scope of the invention.

What is claimed as being new and desired to be protected by LETTERS PATENT of the U.S. is as follows:

1. A new and improved dental travel pack kit which comprises: a resilient plastic pocket-size dental implement carrying case; a plurality of pivotally mounted dental implements fastened therein; and means to permit said dental implements to pivot upwardly from said carrying case and to be locked into such upwardly pivoted position while using said container as the handle for said dental implements, said means to permit said implements to pivot upwardly comprises a tubular pivot member affixed to a base portion of each of said implements and a pivot pin extending through said carrying case and said tubular pivot members to pivotally secure said implements to said case, said carrying case having spaced side walls and said pivot pin extending through said side walls with said pivot pin having a head portion arrayed to project exteriorly of the carrying case when the pivot pin is secured within the carrying case.

2. A travel pack kit as in claim 1 wherein the top of said case is notched to accept said implements pivoted upwardly from said case.

3. A travel pack kit as in claim 1 wherein said carrying case has a hinged face on one side thereof, said face opening at least 90 degrees to said case to permit selection and upward pivoting of a dental implement from within said case.

4. A travel pack kit as in claim 3 wherein said hinged face impinges on said case when in closed position and secures in place a dental implement upwardly pivoted from said case.

5. A travel pack kit as set forth in claim 1 wherein one of said dental implements comprises a brush head, one of said dental implements having a massage tip, and a yet further of said dental implements having a dental floss holder means for holding dental floss.

* * * * *